United States Patent

Xu et al.

(10) Patent No.: US 9,277,926 B2
(45) Date of Patent: Mar. 8, 2016

(54) DRILL SLEEVE

(71) Applicant: Wisconsin Alumni Research Foundation, Madison, WI (US)

(72) Inventors: Kenneth O. Xu, Eden Prairie, MN (US); Austin J. Crow, Madison, WI (US); Joshua M. Kolz, Milwaukee, WI (US); Sarah R. Sandock, Milwaukee, WI (US); John G. Renfrew, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 558 days.

(21) Appl. No.: 13/659,542

(22) Filed: Oct. 24, 2012

(65) Prior Publication Data

US 2014/0114316 A1     Apr. 24, 2014

(51) Int. Cl.
  *A61B 17/00* (2006.01)
  *A61B 17/16* (2006.01)

(52) U.S. Cl.
  CPC ................................ *A61B 17/1633* (2013.01)

(58) Field of Classification Search
  CPC ................... A61B 17/1617; A61B 17/1633
  USPC ........................................................... 606/80
  See application file for complete search history.

(56) References Cited

U.S. PATENT DOCUMENTS

| 4,534,682 | A | 8/1985 | Carlson |
|---|---|---|---|
| 5,071,293 | A | 12/1991 | Wells |
| 5,073,068 | A | 12/1991 | Jinkins et al. |
| 5,180,388 | A | 1/1993 | DiCarlo |
| 5,205,682 | A | 4/1993 | Jinkins |
| 5,330,480 | A | 7/1994 | Meloul et al. |
| 5,380,333 | A | 1/1995 | Meloul et al. |
| 5,895,389 | A | 4/1999 | Schenk et al. |
| 7,357,804 | B2 | 4/2008 | Binder, Jr. et al. |
| 7,488,327 | B2 | 2/2009 | Rathbun et al. |
| 7,731,721 | B2 | 6/2010 | Rathbun et al. |
| 8,029,523 | B2 | 10/2011 | Wallis et al. |
| 8,118,520 | B2 | 2/2012 | Hintze et al. |
| 8,152,809 | B1 | 4/2012 | Kao et al. |
| 8,221,433 | B2 | 7/2012 | Lozier et al. |
| 2006/0219418 | A1* | 10/2006 | Arakawa et al. ........... 173/162.2 |
| 2010/0034605 | A1 | 2/2010 | Huckins et al. |

* cited by examiner

*Primary Examiner* — David Isabella
*Assistant Examiner* — Christine Nelson
(74) *Attorney, Agent, or Firm* — Boyle Fredrickson, S.C.

(57) ABSTRACT

A drill sleeve includes a lower end that engages a bone being drilled with a drill bit of a drill during an orthopedic procedure, an upper end that is movable with respect to the lower end, and a fluid damper between the upper and lower ends for resisting movement of the upper end with respect to the lower end and which may reduce a distance at which a drill bit can plunge through a back side of the bone by increasing resistance to drill movement at occurrence of plunge through the back of the bone. The drill sleeve may include measurement scale and a lock that prevents relative motion of the upper and lower ends after the bone has been drilled for evaluating a position of a depth indicator with respect to the measurement scale that corresponds to a depth of the bore in the bone.

20 Claims, 6 Drawing Sheets

DRILL SLEEVE

STATEMENT REGARDING FEDERALLY SPONSORED RESEARCH OR DEVELOPMENT

N/A

CROSS REFERENCE TO RELATED APPLICATION

N/A

BACKGROUND OF THE INVENTION

The present invention relates to drill sleeves that protect soft tissues during orthopedic drilling procedures.

During orthopedic procedures, when using drills to make bores in bones for internal fixation of fractured bones, overlying soft tissue may become entangled in drill bits rotated by the drills. For procedures that require drilling bores entirely through the bones, the drill bits may plunge through the back sides of the bones and into the soft tissue beyond the bone which may damage neurovascular structures and/or other soft tissue. Regardless, after drilling bores in bones, the depths of the bores need to be measured so that proper length fasteners can be selected for use in the drilled bores. Measuring bore depth is typically done with a depth gauge that requires an additional step after drilling. While measuring a bore that extends entirely through a bone, a hook of the depth gauge may be pushed beyond the backside of the bone so that the hook can be pulled back into engagement with the backside of the bone to measure the bore. Soft tissue beyond the backside of the bone can be contacted by the hook when it is pushed beyond the backside of the bone. After measuring, the hook may again be pushed beyond the backside of the bone to release the engagement between the hook and the backside of the bone to allow withdrawal of the hook through the bore and at which point the soft tissue beyond the back side of the bone may again be contacted with the hook of the depth gauge.

To address these issues, various devices have been utilized. Drill sleeves having rigid tubes through which the drill bits pass allow the drill bit to be delivered to the bone without directly contacting the soft tissue at the entry side of the bone at which the bore is initiated. Specialized drill bits and matched specialized drill sleeves are available that have corresponding markings for showing how far the drill bits have advanced relative to the drill sleeves. Specialized complex drills are available and can include clutching mechanisms that disengage rotating drives under conditions of reduced torque and others which allow for incremental advancing of the drill bits to predetermined distances.

SUMMARY OF THE INVENTION

The present invention provides a drill sleeve that can be used with conventional orthopedic drills and drill bits, and may protect soft tissue beyond the backside of a bone by reducing drill bit travel past the bone during a bone plunge-through event. The drill sleeve is not fixed to the drill which may allow the drill sleeve to be separately sterilized as a unit. The drill sleeve may allow for measurement of bore depth by evaluating a position of a slider-mounted indicator relative to a base-mounted measuring scale of the drill sleeve. A slider of the drill sleeve may be lockable with respect to a base of the drill sleeve to help evaluate the bore depth using the indicator in measuring scale on the drill sleeve, which may allow for precise measurement of bore depth without requiring an additional measurement step with a separate depth gauge, and while using a conventional drill bit.

Specifically then, according to one aspect of the invention, a drill sleeve is provided for use in forming a bore in a bone during an orthopedic procedure and that includes a base for engaging a surface of a bone to be drilled, a slider mounted for movement with respect to the base, and a fluid damper arranged with respect to the base and slider for resisting movement of the slider. Movement of the drill in a drilling direction may move the slider toward the base so that by resisting movement of the slider, the fluid damper correspondingly resists movement of the drill in the drilling direction. The fluid damper may be adapted to increase its resistance in response to an increase in velocity of the drill in the drilling direction.

It is thus a feature of at least one embodiment of the invention to provide a dynamic braking force that acts against an acceleration experienced by the drill bit at the moment of plunge-through, which may reduce the distance at which the drill bit extends beyond the bone during a plunge-through event. It is thus also a feature of at least one embodiment of the invention to prevent over travel of a drill bit during a plunge through event by enhancing a surgeon's ability to manually stop forward momentum of the drill during the plunge through event by way of a passively applied progressive resistive force supplementation.

According to another aspect of the invention, the base, slider, and fluid damper define a unit that is distinct and uncoupled from the drill during use.

It is thus a feature of at least one embodiment of the invention to allow quick tool-less separation of the drill and drill sleeve to accommodate sterilization of the drill sleeve independent from the drill. It is thus also a feature of at least one embodiment of the invention to allow for a plunge-through reducing drill sleeve without requiring a drill-mounted accessory that could add weight to and potentially obstruct view around a standard size and shaped drill with which surgeons may already be comfortable using.

According to another aspect of the invention, the passage of the drill sleeve through which the drill bit is received may be defined within a tube that may extend between the slider and base of the drill sleeve. The tube may include an upper tube segment and a lower tube segment that engage each other and are longitudinally movable with respect to each other so that the tube can telescope to define a variable length during movement of the slider. The tube may extend through a fluid cavity of the fluid damper and a piston that travels through a viscous liquid contained in the fluid cavity may be mounted to the upper tube segment so that the piston travels in unison with the slider.

It is thus a feature of at least one embodiment of the invention to allow a drill bit to pass concentrically through the fluid damper which may provide the drill sleeve as a compact unit that can be easily manipulated and seen around.

According to another aspect of the invention, a chuck of the drill that holds the drill bit may engage the slider so that movement of the drill in the drilling direction pushes the slider toward the base. A bearing may be arranged upon the slider and a cap may be supported for rotation by the bearing and define an interface between the slider of the drill.

It is thus a feature of at least one embodiment of the invention to accommodate rotation of the chuck of the drill at an interface of the slider and the drill so as to avoid reactionary twisting of the drill sleeve by engagement of the drill sleeve with rotating components of the drill.

These particular features, objects, and advantages may apply to only some embodiments falling within the claims and thus do not define the scope of the invention.

DETAILED DESCRIPTION OF THE PREFERRED EMBODIMENT

Figure 1:
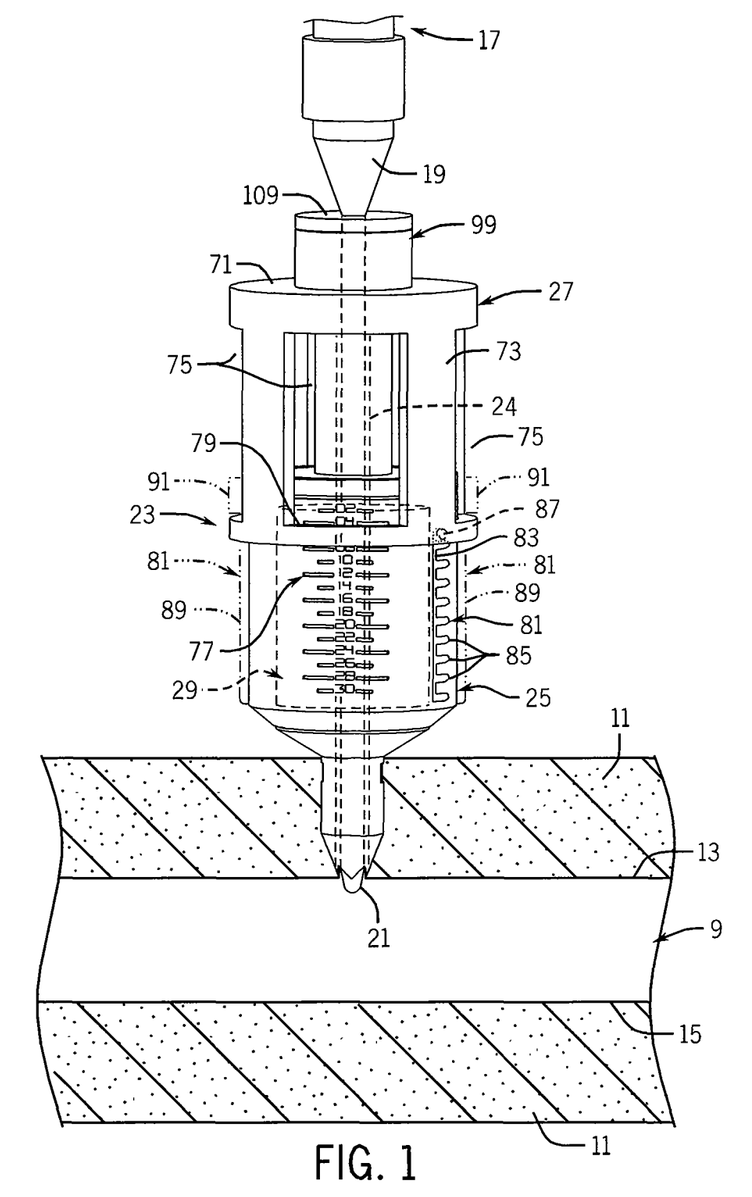
FIG. 1 is a simplified pictorial view of a drill sleeve system.
Figure 2:
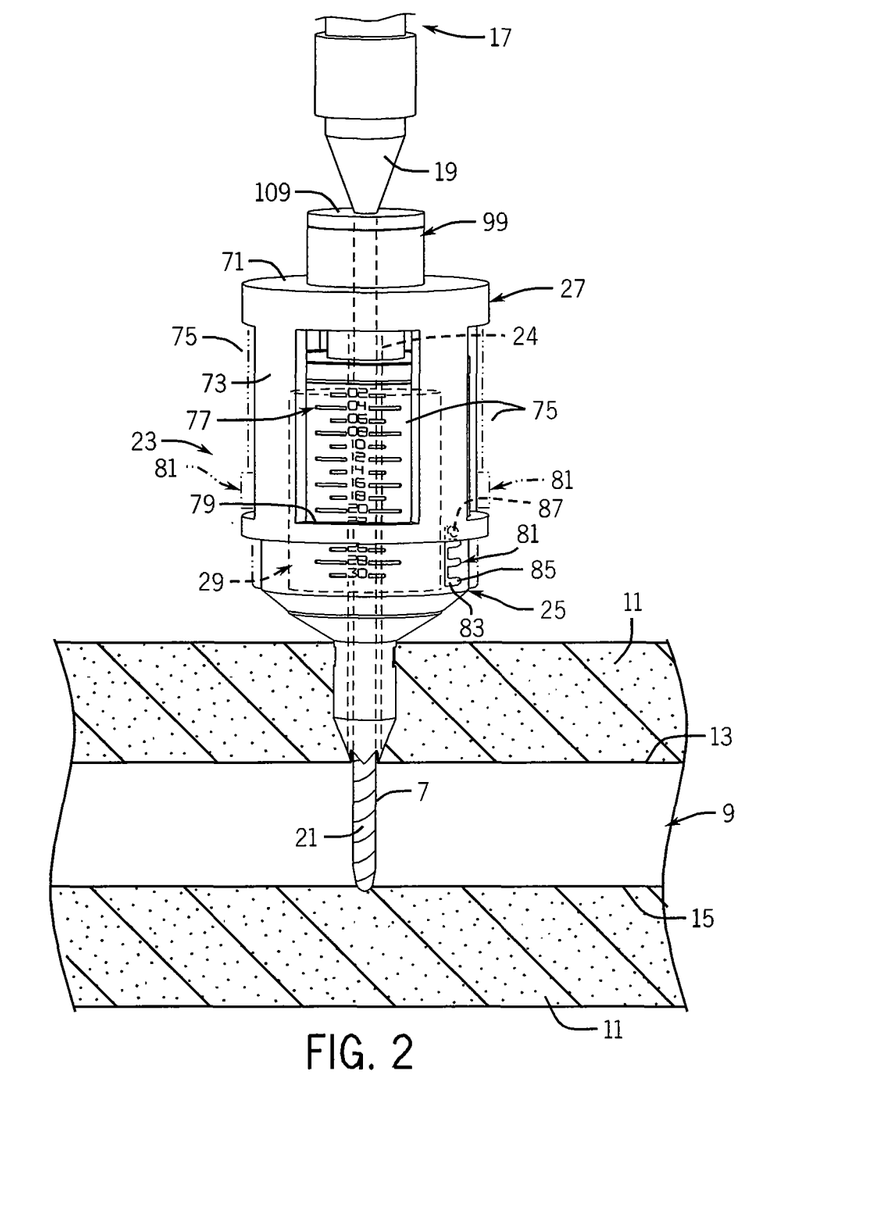
FIG. 2 is another simplified pictorial view of the drill sleeve system of FIG. 1.

Referring now to FIGS. 1 and 2, a drill sleeve system 5 for use in forming a bore 7 (FIG. 2) in a bone 9 during an orthopedic procedure is shown that may protect soft tissue 11 located outwardly of a front side 13 of the bone 9 and a back side 15 of the bone 9. The drill sleeve system 5 may include a drill 17 having a chuck 19 which holds the drill bit 21 that forms the bore 7 and is guided by a drill sleeve 23 that protects the soft tissue 11 and provides a passage 24 through which the drill bit 21 is received. The exemplary procedure schematically represented in FIGS. 1 and 2 is drilling the bore 7 through the entire bone 9, with FIG. 1 showing an event of initiation of forming the bore 7 and FIG. 2 showing an event of plunge through the back side 15 of the bone 9. Although the procedure shown in FIGS. 1 and 2 represents drilling through the entire bone 9 so that bore 7 is formed as a through bore, it is understood that bore 7 may be a blind bore passing through less than the entire thickness of the bone 9 in some orthopedic procedures.

Still referring to FIGS. 1 and 2, the drill sleeve 23 includes a base 25 for engaging a surface of the bone 9 to be drilled, shown at the front side 13 of the bone 9. A slider 27 is mounted to the base 25 so that the slider 27 can move longitudinally with respect to the base 25. During use, slider 27 is engaged by the chuck 19 of the drill 17 so that movement of the drill 17 in the drilling direction toward the base 25 and bone 9 pushes the slider 27 toward that base 25 so as to advance the slider 27 along the base 25. In this way, movement of the drill 17 is translated into movement of the slider 27 in unison with the drill 17 while the base 25 remains in a stationary position as supported by the bone 9. A fluid damper 29 is arranged with respect to the base 25 and slider 27 for resisting movement of the slider 27 and drill 17 relative to the base 25.

Still referring to FIGS. 1 and 2, the base 25, slider 27, and fluid damper 29 may collectively define a unit that is distinct and always uncoupled from the drill 17 so as to accommodate sterilization of the drill sleeve 23 independent from the drill 17, since the drill sleeve 23 may be made from a stainless steel or other autoclavable or readily sterilizable material. The only interactions between the drill 17 and the drill sleeve 23 may be that the drill bit 21 extends through the passage 24 of the drill sleeve 23 and that the chuck 19 interfaces with the slider 27 without the drill sleeve 23 being fixed to the drill 17 in any way. This allows the drill 17 to be separated from the drill sleeve 23 by merely withdrawing the bit 21 from the passage 24. The invention contemplates that the drill sleeve 23 may be temporarily attached to the drill 17, for example by way of an interconnecting brace which may include hardware that allows for tool-less removal of the drill sleeve 23 from the drill 17 to facilitate separation of the drill sleeve 23 from the drill 17, which may allow for sterilization of the drill sleeve 23 independent from the drill 17.

Figure 3:
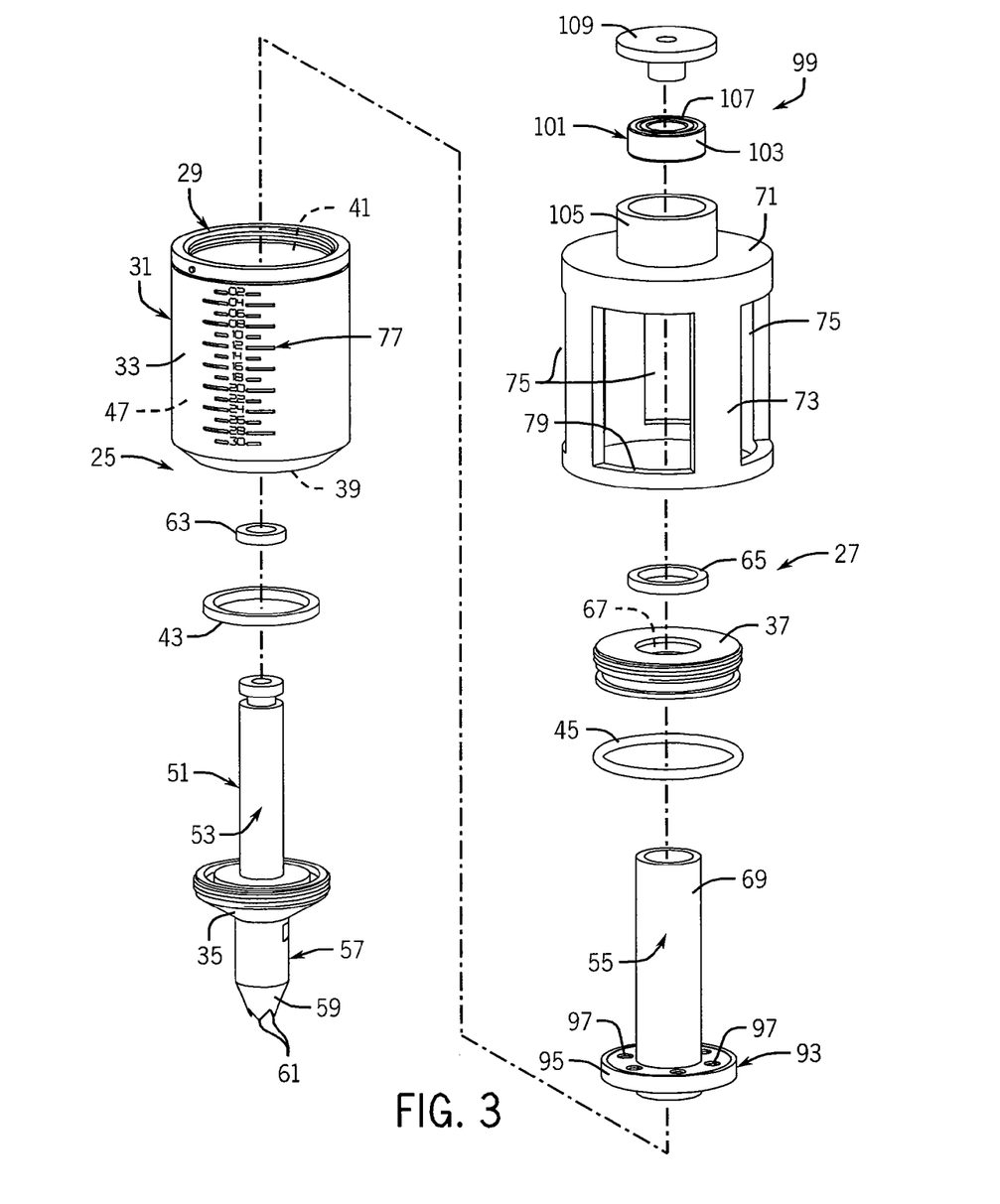
FIG. 3 is an exploded pictorial view of a variant of drill sleeve of FIG. 1.
Figure 4:
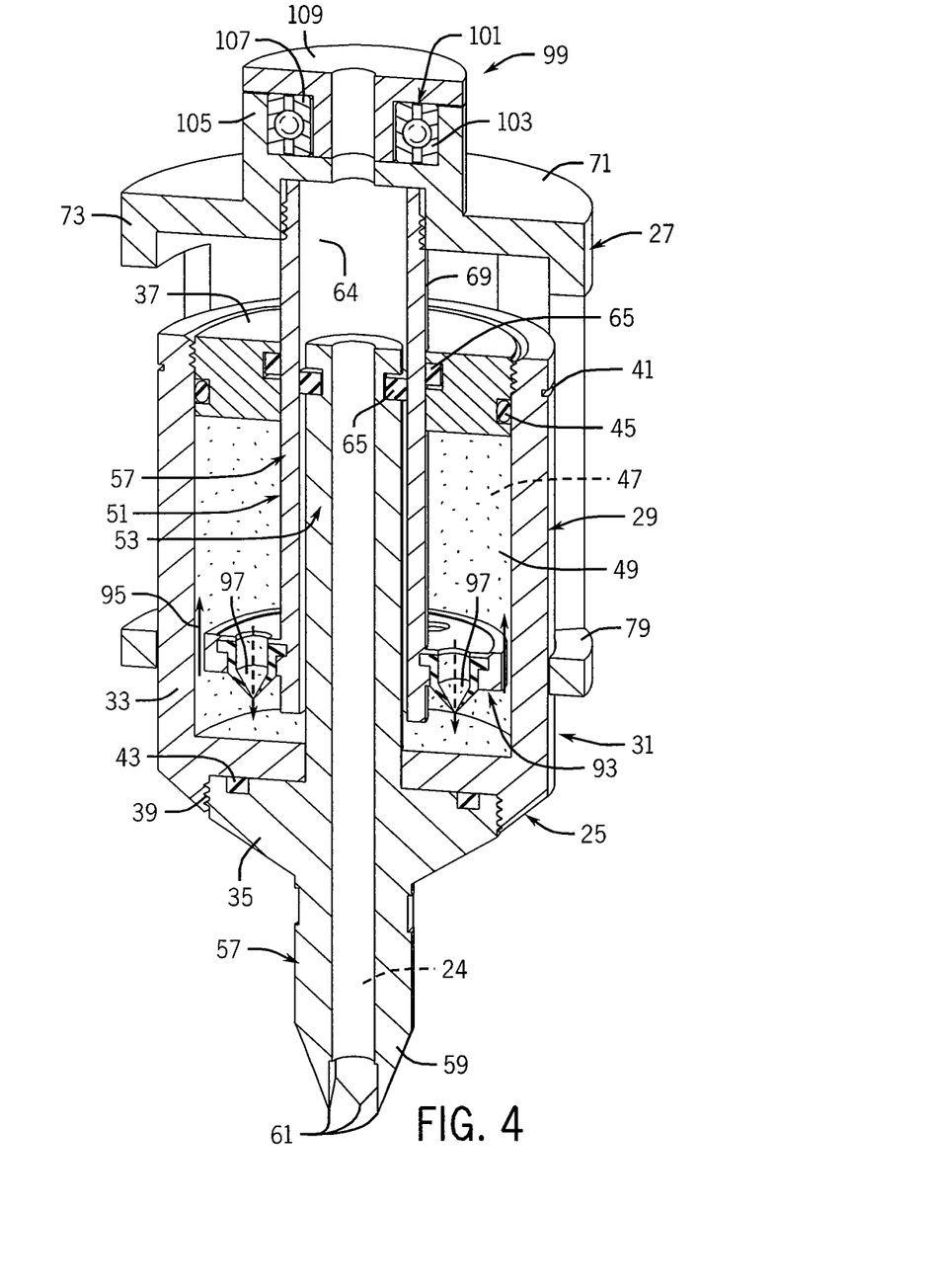
FIG. 4 is a cross-sectional view of the drill sleeve of FIG. 3.

Referring now to FIGS. 3 and 4, the fluid damper 29 may be arranged at least partially within the base 25. The base 25 may provide a container 31 that includes a container side wall 33 having a hollow cylindrical form, a container lower wall 35, and the container upper wall 37. The container side wall 33 provides a lower opening 39 and an upper opening 41. The container lower wall 35 threads in to the lower opening 39, with an o-ring 43 that creates a seal between the container lower wall 35 and the container side wall 33. The container upper wall 37 threads in to the upper opening 41, with an o-ring 45 that creates a seal between the container upper wall 37 in the side wall 33. In this way, a fluid cavity 47 is defined within the container 31. A fluid 49 (FIG. 4) is contained within the fluid cavity 47 cooperating with other components of the fluid damper 29 for resisting movement of the slider 27 and drill 17, as explained in greater detail elsewhere herein. The fluid 49 may be a Newtonian fluid or a non-Newtonian fluid. In some embodiments, the fluid 49 may be a gas or may be a liquid such as water or another relatively lower viscosity liquid. In other embodiments, the fluid 49 may be a relatively higher viscosity liquid, such as an oil, honey, corn syrup, glycerol, or other relatively higher viscosity liquids.

Still referring to FIGS. 3 and 4, the passage 24 is defined by a longitudinally extending through bore of a tube 51. Tube 51 includes a lower tube segment 53 and an upper tube segment 55 that engage each other and are longitudinally movable with respect to each other so that the tube 51 can telescope to define a variable length during movement of the slider 27. The lower tube segment 53 extends upwardly from an upper surface of the container lower wall 35. A post 57 that is coaxially aligned with a lower tube segment 53 extends in an opposite direction from a lower surface of the container lower wall 35, so that the passage 24 extends continuously through the lower tube segment 53 and post 57. Post 57 may include a tip 59 with spikes 61 that may engage and grip the bone 9 (FIGS. 1 and 2). At an upper end of the lower tube segment 53, an o-ring 63 provides a seal between the lower tube segment 53 and an inner circumferential surface 64 of the upper tube segment 55, while allowing the upper tube segment 55 to slide up and down with respect to and concentrically outside of the lower tube segment 53. An o-ring 65 is seated in an opening 67 of the container upper wall 37 and provides a seal between the container upper wall 37 and an outer circumferential surface 69 of the upper tube segment 55, while allowing the upper tube segment 55 to slide up and down with respect to and concentrically inside of the container upper wall 37.

Still referring to FIGS. 3 and 4, an upper end of the upper tube segment 55 is threaded into a slider upper wall 71, whereby the upper tube segment 55 is connected to the slider 27 for movement in unison with the slider 27. This allows the slider 27 to be guided for movement relative to the base 25 at multiple concentrically space interfaces between the base 25 and the slider 27, which may help maintain registration of the slider 27 with respect to the base 25 during movement. Such concentrically spaced interfaces are defined at the interfacing lower and upper tube segments 53, 55 and an interface between a slider side wall 73 and the container side wall 33.

Referring now to FIG. 3, multiple windows 75 extend through the slider side wall 73 so that the windows 75 are circumferentially spaced from each other about the periphery of the slider side wall 73. Each window 75 provides an opening through which a measurement scale 77 that is provided on an outer surface of the container side wall 33 may be viewed. An indicator 79 is provided on the slider side wall 73 for providing showing how far the slider 27 has moved with respect to the base 25. Indicator 79 is shown in this embodiment as being an edge provided at the slider side wall 73 which defines part of the boundary of the window 75, although it is understood that the indicator 79 may be printed indicia or other indicia upon the slider 27.

Referring again to FIGS. 1 and 2, a lock 81 may be arranged on the drill sleeve 23 for preventing relative movement of the slider 27 with respect to the base 25 and at least one direction. The lock 81 may allow for maintaining the slider 27 and base 25 in a constant relative position for determining a depth of the bore 7 by evaluating the measurement scale 77 and indicator 79, even after the drill sleeve 23 has been removed from its engagement with the bone 9. The lock 81, shown in solid line format, includes a groove 83 that extends longitudinally along the container side wall 33 in multiple pockets 85 that are spaced from each other and extend transversely away from the groove 83. A pin 87 may extend from an inner circumferential surface of the slider side wall 73 and into the groove 83 so that the pin 87 may travel up and down the groove 83 and be selectively slid to one of the pockets 85 upon a twisting of the slider 27 relative to the base 25 so as to lock the slider 27 and base 25 with respect to each other. In one embodiment, the pin 87 may be defined by a spring biased ball bearing and the pockets 85 may include depressions that receive the pin 87 to provide a detent-type arrangement. The locks 81, shown in phantom outline form on opposing sides of the drill sleeve 23, may provide a ratcheting-type lock arrangement that may include a track 89 arranged in the base 25 with transversely extending ribs and a ratcheting tab or buckle 91 arranged in the slider 27 that ratchets across the ribs while moving with respect to the track 89 and that can be selectively released to permit free movement between the buckle 91 and track 89.

Referring again to FIGS. 3 and 4, when the lock 81 (FIGS. 1 and 2) is in a disengaged position so as to permit relative movement of the slider 27 with respect to the base 25, a piston 93 travels through the fluid cavity 47 and in unison with the slider 27 so as to resist movement of the slider 27. Movement of the piston 93 through the fluid cavity 47 displaces fluid 49 to flow along a fluid flow path that flows in the opposite direction of the travel direction of the piston 93. As shown in FIG. 4, the piston 93 includes an outer circumferential surface 95 that is radially spaced from an inner circumferential surface of the container side wall 33. This provides an annular clearance through which a flow path is defined along which the fluid 49 flows past the piston 93. As represented by the solid line arrows in FIG. 4 between the piston 93 and the container side wall 33, during an advancing stroke when the piston 93 moves toward the container bottom wall 35, fluid 49 is displaced from a lower portion of the fluid cavity 47 toward an upper portion of the fluid cavity 47 through the annular clearance. It is understood that in some embodiments, the piston 93 includes through bores through which the fluid 49 may flow during and advancing stroke. Regardless, the fluid damper 29 increases its resistance to movement of the slider 27 upon increases in velocity of movement of the slider 27 while the slider 27 moves closer to the base 25, because resistance to movement of the piston 93 through the fluid 49 in the fluid cavity 47 increases during velocity increases of the piston 93 during an advancing stroke.

Still referring to FIGS. 3 and 4, one-way valves 97 are arranged in the piston 93 to allow the fluid 49 to flow through the one-way valves 97 only during a withdrawal stroke in which the piston 93 moves toward the container upper wall 37. The one-way valves 97 of this embodiment are shown as duckbill valves, although it is understood that the one-way valves 97 may be other types of one-way valves, for example, spring-actuated ball-type check valves. Regardless, the one-way valves 97 allow the slider 27 to move relatively more easily during withdrawal strokes away from the base 25, while the slider 27 experiences relatively more resistance to travel during advancing strokes toward the base 25, which may occur when the drill 17 (FIGS. 1 and 2) pushes the slider 27 toward the base 25 while performing a drilling procedure.

Still referring to FIGS. 3 and 4, a bearing arrangement 99 may be provided at the slider upper wall 71 for accommodating the rotation of the chuck 19 and avoiding reactionary twisting of the drill sleeve 23 during use. The bearing arrangement 99 may include a bearing 101 that has an outer race 103 which is seated within a collar 105 that extends upwardly from the slider upper wall 71, and inner race 107 of the bearing 101 can rotate freely with respect to the fixed collar 105. In this embodiment, a cap 109 is mounted to the inner race 107 which allows the cap 109 to also rotate freely with respect to the fixed collar 105. An interface between the chuck 19 of the drill 17 and the slider 27 of the drill sleeve 23 is defined between the engaging upper surface of the cap 109 and a lower surface of the chuck 19. This allows the cap 109 to rotate in unison with the chuck 19, without subjecting the entire drill sleeve 23 to a torque from the rotating chuck 19.

Figure 5:
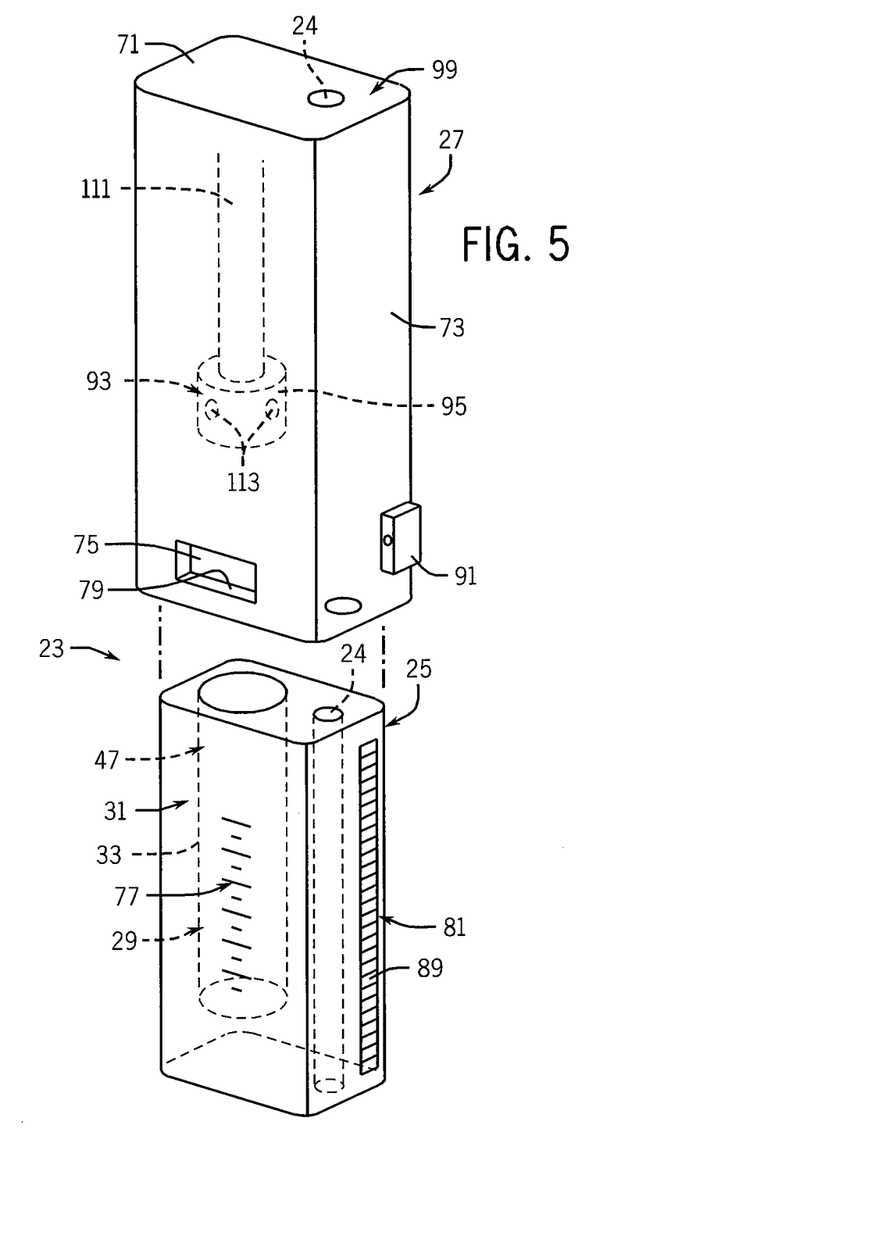
FIG. 5 is a simplified exploded pictorial view of another variant of the drill sleeve of FIG. 1.

Referring now to FIG. 5, the drill sleeve 23 of this embodiment has components that are mostly identical to those described with respect to FIGS. 1-4, whereby such descriptions are applicable here with respect to the drill sleeve 23 of FIG. 5. Unlike the substantially cylindrical drill sleeve 23 of FIGS. 1-4, the drill sleeve 23 of FIG. 5 has a more box-like or overall rectangular configuration. The passage 24 of this embodiment is parallel to but spaced from the fluid damper 29, whereby the drill bit 21 does not pass concentrically through the fluid damper 29 as it did in the embodiments of FIGS. 1-4. A support 111 suspends the piston 93 from the slider upper wall 71 or other portion of the slider 27 so that the piston 93 moves in unison with the slider 27 and is sealed within and housed for movement through the fluid cavity 47 of the container 31. In this embodiment, the bearing arrangement 99 may be defined by material of the slider upper wall 71 which may have a sufficiently low coefficient of friction to permit the chuck 19 to freely rotate and slide against its surface without imposing a reactionary twisting of the drill sleeve 23.

Figure 6:
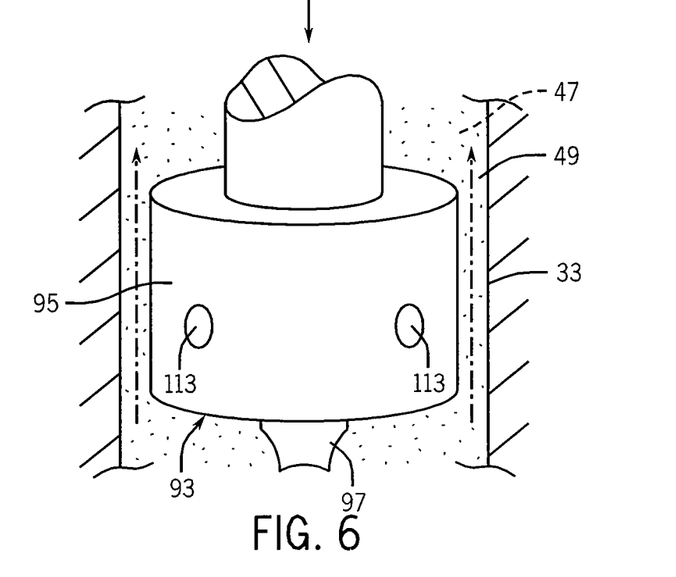
FIG. 6 is a cross-sectional view of a portion of the drill sleeve of FIG. 5.
Figure 7:
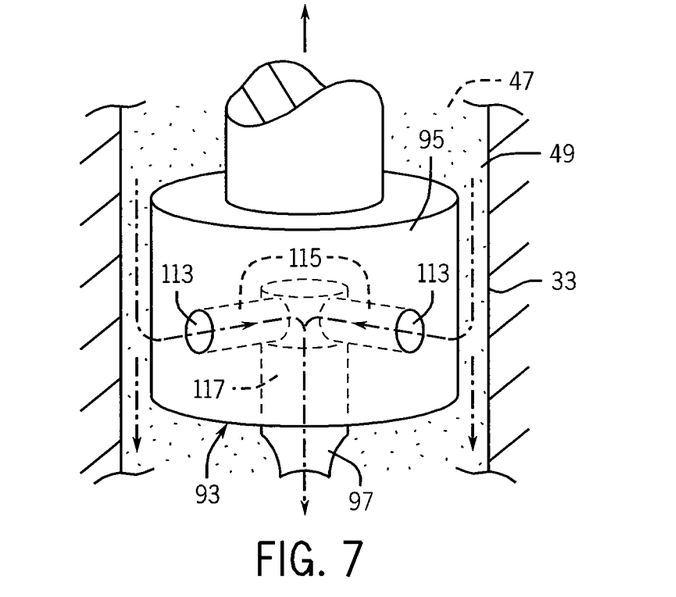
FIG. 7 is another cross-sectional view of a portion of the drill sleeve of FIG. 5

Referring now to FIGS. 5-7, openings 113 that are spaced from each other are defined in the outer circumferential surface 95 of piston 93. As shown in FIG. 7, the openings 113 connect to radially extending bores 115 that connect to an axially extending bore 117 that presents an opening at a bottom surface of the piston 93 and in which the one-way valve 97 is mounted. In this way, during an advancing stroke such as that shown in FIG. 6, the fluid 49 is displaced so as to flow through an annular clearance between the piston 93 and the container side wall 33 while the one-way valve 97 prevents flow of the fluid 49 through the one-way valve 97 during the advancing stroke. This is represented by the dashed line arrows between the piston 93 and the container side wall 33 in FIG. 6.

During a withdrawal stroke such as that shown in FIG. 7, the fluid 49 is displaced so as to flow through the annular clearance between the piston 93 and the container side wall 33 and also through the openings 113 and bores 115, 117 and out the one-way valve 97. This is represented by the dashed line arrows between the piston 93 and the container side wall 33 and also through the openings 113 and bores 115, 117 and one-way valve 97 in FIG. 7 which provides relatively less resistance while the piston 93 travels during a withdrawal stroke rather than during an advancing stroke.

Although the drill sleeve system 5 is described for use in orthopedic procedures, it may be suitable for other uses. Such other used may include dental procedures having tooth material(s) as substrates in which the bores are formed, optionally other drilling procedures for other substrates in which the bores are formed, which may include wood, polymeric, composite, metallic, or other materials.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom", and "side" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

When introducing elements or features of the present disclosure and the exemplary embodiments, the articles "a", "an", "the", and "said" are intended to mean that there are one or more of such elements or features. The terms "comprising", "including", and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A drill sleeve for use in forming a bore in a bone with a drill bit that is rotated by a drill that can move in a drilling direction toward the bone during an orthopedic procedure, the drill sleeve comprising:
a base having a first surface for engaging a surface of a bone to be drilled, the base defining a passage that can receive the drill bit to engage the bone;
a slider having a second surface abutting the drill with movement of the drill in the drilling direction, the slider mounted for movement with respect to the base so that movement of the drill in the drilling direction moves the slider toward the base; and
a fluid damper arranged with respect to the base and slider for resisting movement of the slider, wherein the fluid damper is configured to increase the resistance to the movement of the slider with respect to the base in response to an increase in velocity of the drill in the drilling direction.

2. The drill sleeve of claim 1 wherein the base, slider, and fluid damper define a unit that is distinct and uncoupled from the drill during use so as to accommodate sterilization of the drill sleeve independent from the drill.

3. The drill sleeve of claim 2 wherein the passage that can receive the drill bit is defined within a tube extending between the slider and the base.

4. The drill sleeve of claim 3 wherein the tube includes an upper tube segment and a lower tube segment that engage each other and are longitudinally movable with respect to each other so that the tube can telescope to define a variable length during movement of the slider.

5. The drill sleeve of claim 4 wherein the fluid damper includes a fluid cavity and wherein the upper tube segment is fixed with respect to the slider and includes a piston extending radially from the upper tube segment, the piston arranged for translation within the fluid cavity for resisting movement of the slider and drill.

6. The drill sleeve of claim 2 wherein a chuck of the drill that holds the drill bit engages the slider so that movement of the drill in the drilling direction pushes the slider toward the base.

7. The drill sleeve of claim 6 further including a bearing arranged upon the slider for accommodating rotation of the chuck of the drill at an interface of the slider and the drill.

8. The drill sleeve of claim 7 further including a cap supported for rotation by the bearing and defining the interface between the slider the drill.

9. The drill sleeve of claim 1 further including a measurement scale and an indicator arranged for movement with respect to the measurement scale and in unison with the slider so that a position of the indicator relative to the measurement scale corresponds to a depth of the bore in the bone.

10. The drill sleeve of claim 9 further including a lock that is arranged for preventing movement of the slider relative to the base in a direction that is opposite the drilling direction.

11. The drill sleeve of claim 1 wherein the fluid damper defines a damper stroke length that corresponds to a slider stroke length defined by a distance the slider moves with respect to the base.

12. The drill sleeve of claim 1 wherein the fluid damper comprises a valve arrangement configured to provide:
relatively less resistance to the movement of the slider with respect to the base during a withdrawal stroke of the slider away from the base; and
relatively more resistance to the movement of the slider with respect to the base during an advancing stroke of the slider toward the base.

13. A drill sleeve system for use in forming a bore in a bone during an orthopedic procedure, comprising:
a drill including a drill bit for forming a bore in a bone by moving the drill in a drilling direction during an orthopedic procedure;
a drill sleeve engaging the drill and defining a passage through which the drill bit may extend to engage the bone and including,
a base for engaging a surface of a bone to be drilled with the drill;
a slider movable with respect to the base defining a telescoping portion of the drill sleeve at portions of the base and the slider that are arranged in an at least partially overlapping relationship with respect to each other during telescoping movement of the telescoping portion of the drill sleeve and wherein the slider is arranged with respect to the drill so that movement of the drill is translated into movement of the slider with respect to the base during telescoping movement of the telescoping portion of the drill sleeve; and a fluid damper defined within the telescoping portion of the drill sleeve and arranged with respect to the base and slider for resisting movement of the slider and drill relative to the base, wherein the fluid damper is configured to increase the resistance to the movement of the slider with respect to the base during telescoping movement of the telescoping portion of the drill sleeve in response to an increase in velocity of the drill in the drilling direction.

14. The drill sleeve system of claim 13 wherein the drill and drill sleeve are uncoupled from each other during engagement of the slider and the drill so as to accommodate separation of the drill sleeve and the drill for sterilization of the drill sleeve separate from the drill.

15. The drill sleeve system of claim 14 wherein the passage of the drill sleeve extends parallel to a longitudinal axis of the fluid damper.

16. The drill sleeve system of claim 15 wherein the passage of the drill sleeve extends longitudinally through the fluid damper.

17. The drill sleeve system of claim 16 wherein the passage of the drill sleeve extends through a central portion of the fluid damper.

18. The drill sleeve system of claim 14 wherein the passage of the drill sleeve is defined within a tube that includes an upper tube segment and a lower tube segment that engage each other and are longitudinally movable with respect to each other so that the tube can telescope to define a variable length during movement of the slider.

19. The drill sleeve system of claim 18 wherein the fluid damper includes a fluid cavity and wherein the upper tube segment is fixed with respect to the slider and includes a piston extending radially from the upper tube segment, the piston arranged for translation within the cavity for providing the resistance to movement of the slider and drill.

20. The drill sleeve of claim 13 wherein the fluid damper comprises a valve arrangement in the telescoping portion of the drill sleeve, the valve arrangement configured to provide:

relatively less resistance to the movement of the slider with respect to the base during a withdrawal stroke of the telescoping portion of the drill sleeve corresponding to the slider moving away from the base; and relatively more resistance to the movement of the slider with respect to the base during an advancing stroke of the telescoping portion of the drill sleeve corresponding to the slider moving toward the base.

* * * * *